United States Patent [19]

Toth

[11] Patent Number: 4,600,698
[45] Date of Patent: Jul. 15, 1986

[54] IMMUNOLOGICAL LATEX AGGLUTINATION IN PRESENCE OF CERTAIN LACTONES OR LACTAMS

[75] Inventor: Tibor Toth, Marburg, Fed. Rep. of Germany

[73] Assignee: Hoechst Aktiengesellschaft, Fed. Rep. of Germany

[21] Appl. No.: 575,403

[22] Filed: Jan. 30, 1984

[30] Foreign Application Priority Data

Jan. 31, 1983 [DE] Fed. Rep. of Germany ....... 3303083

[51] Int. Cl.$^4$ .................. G01N 33/546; G01N 33/76
[52] U.S. Cl. ................................. 436/534; 436/510; 436/533; 436/814; 436/818; 436/825
[58] Field of Search ............. 436/533, 534, 510, 818, 436/825, 814

[56] References Cited

U.S. PATENT DOCUMENTS

| | | | |
|---|---|---|---|
| 4,003,988 | 1/1977 | Hoff | 436/818 X |
| 4,060,597 | 11/1977 | Sato et al. | |
| 4,208,187 | 6/1980 | Givner | 436/825 X |
| 4,270,923 | 6/1981 | Kondo | 436/818 X |
| 4,292,038 | 9/1981 | Kondo | 436/825 X |
| 4,315,908 | 2/1982 | Zer et al. | |
| 4,362,531 | 12/1982 | de Steenwinkel | 436/825 X |

*Primary Examiner*—Sidney Marantz
*Attorney, Agent, or Firm*—Finnegan, Henderson, Farabow, Garrett & Dunner

[57] ABSTRACT

A latex agglutination procedure for detecting and determining one of the participants in an antigen-antibody reaction, in which non-specific reactions are suppressed by additives, and an agent for carrying out this type of procedure are described.

8 Claims, No Drawings

IMMUNOLOGICAL LATEX AGGLUTINATION IN PRESENCE OF CERTAIN LACTONES OR LACTAMS

The invention relates to a latex agglutination procedure for detecting or determining one of the participants in an antigen-antibody reaction in the presence of an additive which prevents interference by non-specific reactions, and to an agent suitable for this purpose.

Because of their high specificity and sensitivity, immunological methods of diagnosis have increasingly been used in recent time. Of these methods, the latex agglutination reaction, in which the latex particles are loaded eihter with an antigen or with an antibody, has the advantage that manipulation is very straightforward and the results can be obtained in a short time.

These methods can lead to faulty diagnoses because substances not taking part in the reaction but contained in the urine or in the body fluids, such as sera, plasma or synovia, can cause non-specific agglutination reactions. In order to remove interfering factors of these types, samples of urine, for example for pregnancy tests, are filtered through cellulose filter paper, absorbent cotton, cellulose acetate, polyacrylonitrile, carboxymethylcellulose or other fibrous materials. However, none of these materials is completely satisfactory. For example, it is true that filter paper and absorbent cotton are able to remove substances causing turbidity, but they have the disadvantage that HCG, which is to be determined, is also absorbed.

German Offenlegungsschrift No. 2,951,672, published on July 3, 1980, discloses the pretreatment of fluids which are under investigation with fibers of a cation exchanger resin of the carboxylic acid type. However, suitable fibers are difficult to prepare.

German Offenlegungsschrift No. 3,002,973 contains a description of a latex agglutination reaction carried out in the presence of a urea or formamide derivative. It is true that the latter are able to reduce the abovementioned difficulties, but they are unable to eliminate them.

It has now been found, surprisingly, that the abovementioned technical difficulties can be prevented by carrying out the latex agglutination reaction in the presence of a compound of the general formula I

in which
X is O or NH, and
n is 2–9.

Thus the invention relates to a latex agglutination procedure for detecting or determining a participant in an antigen-antibody reaction using the corresponding participant, which procedure comprises allowing the participants to react together in the presence of a compound of the formula I with the definitions indicated.

Examples of suitable compounds are: butyrolactone, valerolactone, caprolactone, pyrrolidone, valerolactam and caprolactam. A high dipole moment and good dissolving properties, as are possessed by butyrolactam (pyrrolidone), are an advantage. The compounds can be used alone or in combinations. The combinations butyrolactone/pyrrolidone and pyrrolidone/caprolactam are particularly advantageous.

The invention can be used for all reactions based on latex agglutination for detecting immunologically active substances which can be present in body fluids, such as, for example, serum, plasma or synovia and, in particular, in urine. The following may be mentioned as examples of the immunologically active substances to be determined: serum proteins, such as myoglobin, hemoglobin, $\beta_2$-microglobulin and $\alpha_1$-microglobulin, hormones such as HCG (human chorionic gonadotropin), or amylase. The compounds according to formula I can be incorporated in the latex agglutination reaction system by adding them to the diagnostic agent which contains the latex particles loaded with one of the participants in an immunological reaction, or they can be mixed, where appropriate in a solvent, into the test sample.

All latices which are suitable for the latex agglutination test are suitable as latex particles which are loaded with an immunologically active substance. The following may be mentioned as examples: latices of homopolymers and copolymers of styrene or its derivatives, such as methylstyrene, ethylstyrene or chlorostyrene, of acrylic acid or its esters, such as methyl acrylate or ethyl acrylate, of methacrylic acid or its derivatives, such as ethyl methacrylate, acrylonitrile or acrylamide, of dienes, such as butadiene, chloroprene or isoprene, or of vinyl chloride, vinylidene chloride or vinyl acetate. Of these, the latices of the homopolymers or copolymers of styrene, acrylic acid or methyl methacrylate are used with advantage. Latices with a particle size from about 0.1 to about 1 μm, in particular particles with a size from about 0.1 to about 0.6 μm, are preferred.

It is possible to load the latex particles with an immunologically active substance, that is to say an antigen or antibody, using a known method. The conditions vary, depending to a certain extent on the physicochemical properties of the loading substance and the latex particles. When, for example, the latex particles are to be loaded with an antibody, an advantageous procedure is as follows: a gamma-globulin fraction is precipitated in a customary manner from an antiserum containing this antibody, and is dissolved, at a concentration of 0.01 to 4 g/100 ml, in a 0.005 to 0.2 molar buffer having a pH of 7 to 9. The buffer which is advantageously used is a glycine/NaCl, phosphate, imidazole or borate buffer. A 0.15 mole/liter glycine/NaCl buffer solution of pH 8.2 is preferred. A suspension of latex particles at a concentration of 0.1 to 10 g/100 ml is added to the gamma-globulin solution and the mixture is allowed to stand or is stirred at room temperature for 1 to 6 hours or at 35° to 56° C. for 0.5 to 3 hours. The suspension is then centrifuged.

The latex particles loaded with antibodies or antigen are suspended in a buffer solution, preferably a glycine/sodium chloride or imidazole buffer solution, in particular a 0.1 to 0.3 molar imidazole buffer solution, which can contain 1 to 30 g/100 ml, preferably 10 to 15 g/100 ml, of a compound of the formula I, so that the preferred concentration obtained is 0.6 to 1.2 g of latex in 100 ml of suspension.

It is also possible to add a compound of the formula I to the fluid to be tested. Where appropriate, it is also possible to use a solvent for the compound of the formula I.

The examples which follow illustrate the invention.

EXAMPLE 1

(a) A latex reagent which had been produced in accordance with the state of the art and which contained, as the specific antibodies, rabbit antibodies against HCG obtained by immunoadsorption (latex-HCG reagent) was employed in the test below (1c). The sensitivity of the reagent was adjusted to 0.5 to 1 IU/ml using a standard.

(b) 8 g of pyrrolidone and 7 g of butyrolactone were dissolved in 100 ml of 0.2 molar imidazole buffer solution, pH 8.2.

(c) 1 drop (50 μl) of undiluted urine for test was placed in a well of a test plate. 25 μl of solution from (1b) and 25 μl of latex-HCG reagent were added. After thoroughly mixing with a stirring rod, the test plate was moved in a rotatory manner and checked for agglutination after 3 minutes.

EXAMPLE 2

(a) The latex reagent was prepared as (1a).

(b) 5 g of caprolactam and 12 g of pyrrolidone were dissolved in 100 ml of 0.15 molar glycine/NaCl buffer solution.

(c) 1 drop (50 μl) of undiluted urine for test was placed in a well of a test plate. 25 μl of solution from (2b) and 25 μl of latex-HCG reagent were added. After thoroughly mixing with a stirring rod, the test plate was moved in a rotatory manner and checked for agglutination after 3 minutes.

| Number of samples | HCG content | Origin | Number of pos. samples state of the art* | according to the invention |
|---|---|---|---|---|
| 3 | 0 | men | 1 | 0 |
| 2 | 0 | non-pregnant women | 1 | 0 |
| 5 | + | pregnant women** | 5 | 5 |

*Suspension of loaded latex particles in glycine/NaCl buffer without compound of the formula I
**Confirmed pregnancies The table shows that the reagent according to the state of the art gave 2 false positive results in 5 samples (3 from men and 2 from non-pregnant women), while no false positive results were found with the procedure according to the invention.

I claim:

1. A latex agglutination procedure for detecting or determining a participant in an antigen-antibody reaction using the corresponding participant, which procedure comprises allowing the participants to react together in the presence of a compound of the formula I

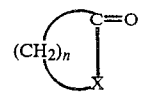

in which
X is O or NH, and
n is an integer from 2-9.

2. The procedure as claimed in claim 1, wherein the compound of the formula I is butyrolactone, valerolactone, caprolactone, pyrrolidone, valerolactam or caprolactam.

3. The procedure according to claim 1 for detecting human chorionic gonadotropin.

4. A latex agglutination procedure for detecting or determining a participant in an antigen-antibody reaction using the corresponding participant, which procedure comprises allowing the participants to react together in the presence of a mixture of compounds of the formula I

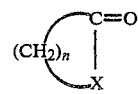

in which X is O or NH and n is an integer from 2-9.

5. The procedure as claimed in claim 4, wherein said mixture comprises compounds selected from the group consisting of butyrolactone, valerolactone, caprolactone, pyrrolidone, valerolactam, and caprolactam.

6. The procedure as claimed in claim 4, wherein said mixture comprises butyrolactone and pyrrolidone.

7. The procedure as claimed in claim 4, wherein said mixture comprises pyrrolidone and caprolactam.

8. The procedure according to claim 4 for detecting human chorionic gonadotropin.

* * * * *

UNITED STATES PATENT AND TRADEMARK OFFICE
CERTIFICATE OF CORRECTION

PATENT NO. : 4,600,698

DATED : July 15, 1986

INVENTOR(S) : Tibor Toth

It is certified that error appears in the above-identified patent and that said Letters Patent is hereby corrected as shown below:

On the first page of the patent, change the designation of assignee from "HOECHST AKTIENGESELLSCHAFT" to --BEHRINGWERKE AKTIENGESELLSCHAFT--.

Signed and Sealed this

Thirtieth Day of December, 1986

Attest:

DONALD J. QUIGG

Attesting Officer

Commissioner of Patents and Trademarks